United States Patent [19]

Kreger et al.

[11] Patent Number: 5,436,564
[45] Date of Patent: Jul. 25, 1995

[54] BIO-POTENTIAL SIGNAL PROCESSOR FOR MAGNETIC RESONANCE IMAGING

[75] Inventors: Kevin S. Kreger, Milwaukee; Charles R. Giordano, Waukesha, both of Wis.

[73] Assignee: General Electric Company, Milwaukee, Wis.

[21] Appl. No.: 908,599

[22] Filed: Jun. 30, 1992

Related U.S. Application Data

[63] Continuation of Ser. No. 563,176, Aug. 6, 1990, abandoned.

[51] Int. Cl.$^6$ .............................................. G01R 33/28
[52] U.S. Cl. .................................. 324/322; 324/318; 128/653.5
[58] Field of Search ............... 324/322, 318, 307, 309, 324/300, 313, 314, 601; 128/653.2, 653.5

[56] References Cited

U.S. PATENT DOCUMENTS

| | | | |
|---|---|---|---|
| 4,093,911 | 5/1978 | Hill et al. | 324/322 |
| 4,649,505 | 3/1987 | Zinser, Jr. et al. | 358/36 |
| 4,675,658 | 6/1987 | Anderson et al. | 340/572 |
| 4,793,361 | 12/1988 | DuFault | 128/696 |
| 4,991,580 | 2/1991 | Moore | 128/653 SC |
| 4,991,587 | 2/1991 | Blakeley et al. | 128/653 A |
| 4,998,058 | 3/1991 | Toft et al. | 324/67 |
| 5,038,785 | 8/1991 | Blakeley et al. | 128/653 A |

FOREIGN PATENT DOCUMENTS

0429190  5/1991  European Pat. Off. .

OTHER PUBLICATIONS

IEEE Transactions on Bio-Medical Engineering, vol. BME 30, No. 7, Jul. 1983, New York, pp. 392-398.
Magnetic Resonance in Medicine, vol. 6, No. 2, Feb. 1988, Duluth Minn., pp. 240-245.
Computer in Cardiology, Sep. 1987, Leuven, Belgium, pp. 541-544.
Yelderman, M. et al., "ECG Enhancement by Adaptive Cancellation of Electro-Surgical Interference", IEEE Transactions on Biomedical Engineering, vol. pp. 392-398, 183.
Windrow, B. and Winter, R., "Neural Networks for Adaptive Filtering and Adaptive Pattern Recognition", IEEE Transactions on Computer Engineering, 1988.
Webster, J. G., "Reducing Motion Artifacts and Interference in Biopotential Recording", IEEE Transactions on Biomedical Engineering, 1984.

*Primary Examiner*—Sandra L. O'Shea
*Assistant Examiner*—Raymond Y. Mah
*Attorney, Agent, or Firm*—Quarles & Brady

[57] ABSTRACT

An adaptive filtering system is used to reduce the electrical noise on low power ECG signals and the like as generated by rapidly switched magnetic gradient fields in magnetic resonance imaging. A correlated noise reference signal is derived from the inputs to the gradient coils by a combination differentiator and low pass filter. The noise reference signal is received by a filter having adjustable coefficients and the result subtracted from the low power signal to produce an error signal used to adjust the coefficients of the filter. Three separate adaptive filters may be placed in series each with a separate correlated noise reference signal to reduce the noise from three gradient coils.

2 Claims, 4 Drawing Sheets

BIO-POTENTIAL SIGNAL PROCESSOR FOR MAGNETIC RESONANCE IMAGING

This application is a continuation of application Ser. No. 07/563,176, filed Aug. 6, 1990, (now abandoned).

BACKGROUND OF THE INVENTION

1. Field of the Invention

The field of the invention is magnetic resonance imaging systems and, in particular, signal processors associated with such equipment for monitoring bio-potential signals.

2. Background Art

Magnetic resonance imaging ("MRI") has developed as an important tool in diagnostic medicine In an MRI "scan", a body being imaged is held within a uniform magnetic field oriented along a z axis of a Cartesian coordinate system. The spins of the nuclei of the body are excited into precession about the z axis by means of a radio frequency (RF) pulse and the decaying precession of the spins produces an NMR signal. The amplitude of the NMR signal is dependent, among other factors, on the number of precessing nuclei per volume within the imaged body termed the "spin density".

Magnetic gradient fields $G_x$, $G_y$, and $G_z$ are applied along the x, y and z axes by means of gradient coils driven by a gradient amplifier system, so as to impress position information onto the NMR Signals through phase and frequency encoding, as is understood in the art. A set of NMR signals may be "reconstructed" to produce an image along a slice through the body. Each set of NMR signals is comprised of many "views", a view being defined as one or more NMR signal acquisitions made under the same x and y gradients fields.

Frequently it is desired to measure certain bio-potential signals, most notably the electrocardiogram signal ("ECG"), during an MRI scan. Such measurements may be required to monitor the status of critically ill patients or to synchronize the acquisition of MRI data with certain physiological phenomenon such as the beating of the heart. Bio-potential signals are intrinsically of low power and hence susceptible to electrical interference. In an MRI system, this interference comes principally from the previously discussed gradient fields when they are switched on and off during the MRI scan.

In order to reduce the interference from such external sources it is customary to filter the bio-potential signal with a low pass filter. For an ECG signal, the principle energy is below 100 Hz and hence a low pass filter having a cut-off frequency in this neighborhood is chosen. Unfortunately, depending on the imaging sequence used, the switching of the gradient fields also may produce significant interference below 100 Hz, thus limiting the effectiveness of the filtering.

Alternatively, the MRI scan may be "gated" and the bio-potential signal processed only for periods occuring during the times that the gradients were not being switched. The principle drawback to this gating method is that the bio-potential signal is still not available for periods of gradient switching and "continuous" measurements, such as that of heart rate for ECG, are therefore difficult to determine. Further, for rapid imaging techniques such as those to produce moving pictures of biological activity ("cine techniques"), the gradient activity is essentially continuous, providing no period for acquiring of the bio-potential during the MRI scan.

SUMMARY OF THE INVENTION

The present invention uses adaptive filtering to reduce the electrical noise caused by gradient switching and the like on low powered bio-potential signals. The key to this technique is the production of noise correlated signals and the arrangement of the adaptive filters to accommodate multiple noise sources.

Specifically, a noise reference signal, related to the electromagnetic fields produced by MRI system, is processed by a filter having adjustable filter coefficients to produce a filtered noise reference signal. This filtered noise reference signal is subtracted from the bio-potential signal to produce an output signal and the output signal is used for adjusting the coefficients of the filter so as to minimize the output signal.

It is one object of the invention to permit the continuous acquisition of low power bio-potential signals in the presence of rapidly switched electromagnetic fields. The subtraction of a filtered noise reference signal from the bio-potential signal effectively reduces the additive electrical noise from the switched fields. The continuous adjustment of the filter coefficients accommodates changes in the switched fields with different imaging sequences.

In one embodiment of the invention, the noise reference signal is produced from the input signals to the MRI coils. These input signals may be differentiated to approximate better the noise induced by the electromagnetic fields.

It is another object of the invention to provide a noise reference signal correlated to the switched fields without the need for separate pick-up coils to measure the induced noise. The inputs to the MRI coils may be used to determined the induced electrical noise and are readily available.

In one embodiment, separate noise reference signals are produced for each coil and filtered by filters associated with each coil. The bio-potential signal is processed by three summing junctions each receiving a filtered noise reference signal from one coil, and the filter coefficients of the associated filter are adjusted separately to minimize the output of each summing junction. The summing junctions may be arranged in series to filter the bio-potential signal.

It is thus another object of the invention to provide an improved method of filtering a bio-potential signal subject to multiple noise sources. It has been determined that the use of separately adjusted filters associated with each coil provides superior filtering of noise when compared to a single filter receiving a composite noise reference signal.

Other objects and advantages besides those discussed above shall be apparent to those experienced in the art from the description of a preferred embodiment of the invention which follows. In the description, reference is made to the accompanying drawings, which form a part hereof, and which illustrate an example of the invention. Such example, however, is not exhaustive of the various alternative forms of the invention, and therefore reference is made to the claims which follow the description for determining the scope of the invention.

DETAILED DESCRIPTION OF THE PREFERRED EMBODIMENT

Figure 1:
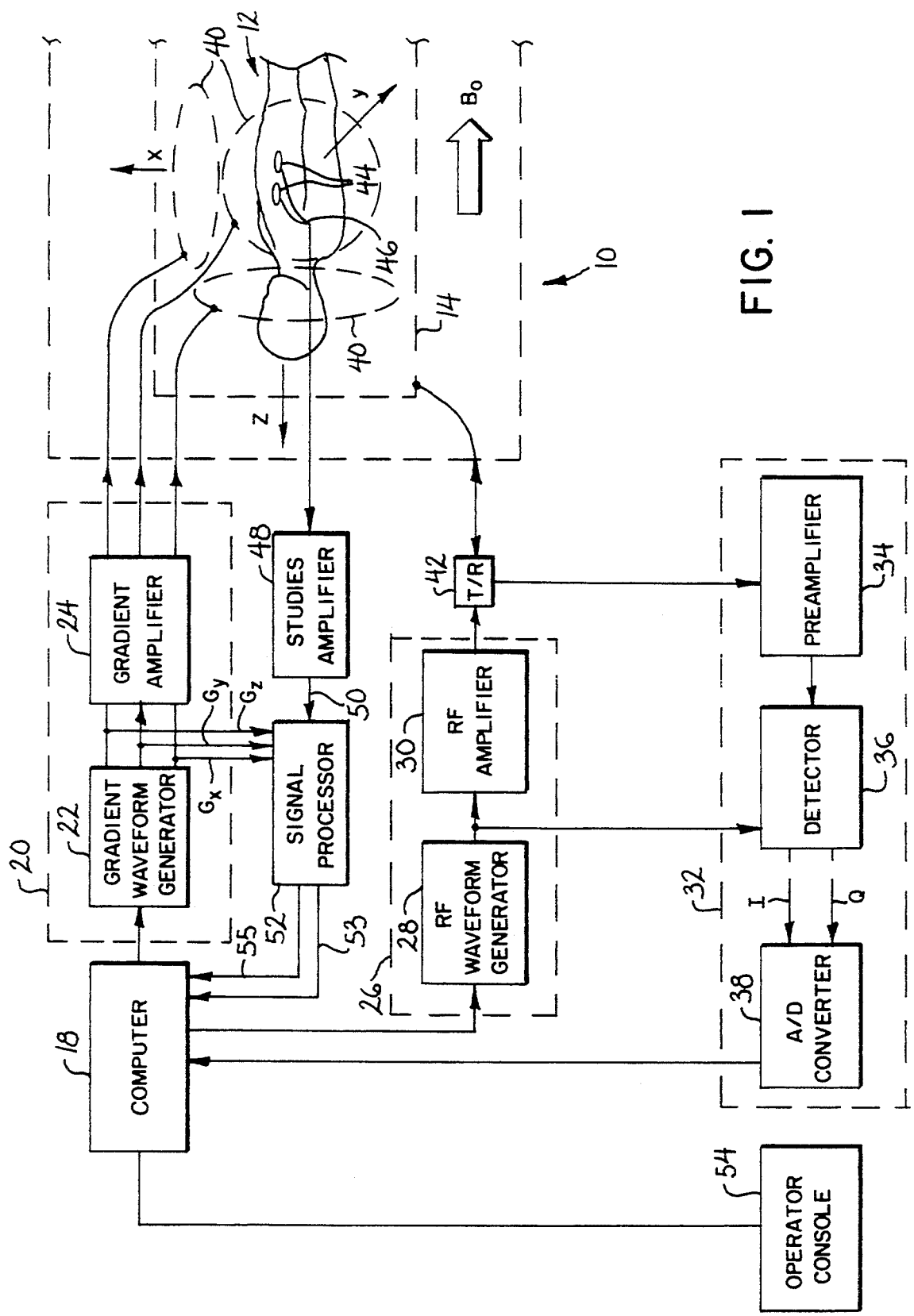
FIG. 1 is a block diagram of an magnetic resonance imaging system showing the relationship of the signal processor of the present invention to the other components of the MRI system.

Referring to FIG. 1, an NMR imaging system includes a magnet 10 to provide a field $B_0$ for polarizing the nuclear spins of an imaged patient 12. An RF coil 14, provides for both the transmission of the RF stimulating pulses, e.g. 90° and/or 180° RF pulses, and for the receiving of the NMR signal as previously described.

A computer 18 provides general control of the MRI system producing timing sequences for control of a gradient signal chain 20, including gradient waveform generator 22 and gradient amplifiers 24; and an RF signal chain 26 including RF waveform generator 28 and RF amplifiers 30; and provides for reception of the sampled and digitized NMR signal from the signal acquisition chain 32, including preamplifier 34, detector 36 and A/D converter 38, for processing and image reconstruction.

The computer 18 provides waveform timing and waveshapes to the gradient waveform generator 22 which produces digital waveform signals $G_x$, $G_y$, and $G_z$. These waveform signals are converted to analog gradient signals by the gradient amplifiers 24 which also boost the power of the waveform signals to drive the gradient coils 40. The waveform signal associated with each gradient coil 40 may be separately controlled. The waveform signals $G_x$, $G_y$, and $G_z$ have carefully limited amplitudes and rise times so that there is an almost exact correspondence between the waveform signals input to the gradient amplifiers 24 and the current in the gradient coils 40.

The computer 18 also provides timing, shape, frequency, phase, and total power information to the RF waveform generator 28 so as to provide the 90° or 180° RF pulse signal described above. The RF pulse signal is boosted by RF amplifier 30 and coupled to RF coil 14 through the transmit/receive switch 42 so as to excite the nuclei of the patient 12 as has been described.

The generated NMR signal also is received by the RF coil 14, which is connected through the transmit/receive switch 42, to preamplifier 34 which provides amplification of the acquired signal. Preamplifier 34 is followed by a quadrature detector 36 which extracts amplitude and phase information from the NMR signal by comparing the input signal to sine and cosine reference local oscillators and producing an in phase (I) and quadrature phase (Q) amplitude signals. The quadrature detector 36 provides the I and Q signals to A/D converter 38. The I and Q signals are filtered and converted into digital form by the A/D converter 38 and transmitted to the computer 18 for image reconstruction through techniques known in the art.

The patient may be monitored by means of electrodes 44 connected by flexible leads 46 to a studies amplifier 48. The studies amplifier 48 incorporates a low pass filter (not shown) to eliminate noise reference signals outside of the bandwidth of the monitored bio-potential signal and incorporates a high speed A/D converter (not shown) to provide a digital bio-potential signal 50 for input to a signal processor 52. As discussed, this bio-potential signal 50 generally includes additive noise from the switched gradient fields from the gradient coils 40. The signal processor 52 also receives the digital waveform signals $G_x$, $G_y$, and $G_z$ from the gradient waveform generator 22. The signal processor 52 reduces the additive noise on the bio-potential signal 50, as will be described, to produce a digital output signal 53 that is received by computer 18 for display on console 54. In addition, bio-potential signal 50 may be received by the signal processor 50 to produce gating pulses 55 which demarcate the peaks of the ECG waveform and which are received by computer 18 and used to synchronize the gradient activity.

Figure 2:
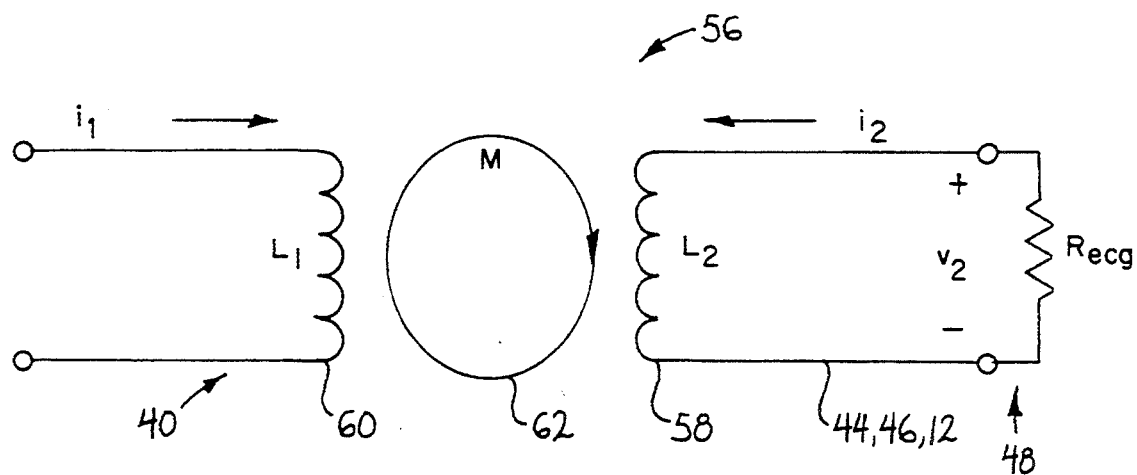
FIG. 2 is a schematic representation of the inductive model of the environment of the ECG signal.

Referring to FIG. 2, the relationship between the additive noise on the bio-potential signal 50 and the waveform signals $G_x$, $G_y$, and $G_z$ may be determined by reference to a model composed of two inductors 58 and 60 linked by a flux path 62 to have a mutual inductance M. The first inductor 60 represents one gradient coil 40 which receives a current $i_1$ equal to a waveform signal $G_x$, $G_y$, or $G_z$. The inductance of the gradient coil 40 is designated $L_1$ and is about 1 mH.

The second inductor 58 is the circuit path formed by the flexible leads 46, the electrodes 44 and the patient 12. The current through this second inductor 58 is $i_2$ which produces a voltage $v_2$ across a series resistance $R_{ecg}$ representing the input resistance of the studies amplifier 48 which is approximately 5 MΩ.

Analyzing this model:

$$v_2 = M\frac{di_1}{dt} + L_2\frac{di_2}{dt} \qquad (1)$$

or $$v_2 \approx M\frac{di_1}{dt} \qquad (2)$$

because $i_1 >> i_2$.

Hence the induced noise voltage input to the studies amplifier 48 is related to the derivative of the waveform signals $G_x$, $G_y$, or $G_z$ and noise on the bio-potential signal 50, as subsequently filtered by the studies amplifier 48, will be related to the derivative of the waveform signals $G_x$, $G_y$, or $G_z$ filtered by a low pass filter equivalent to that incorporated into the studies amplifier 48.

Figure 3:
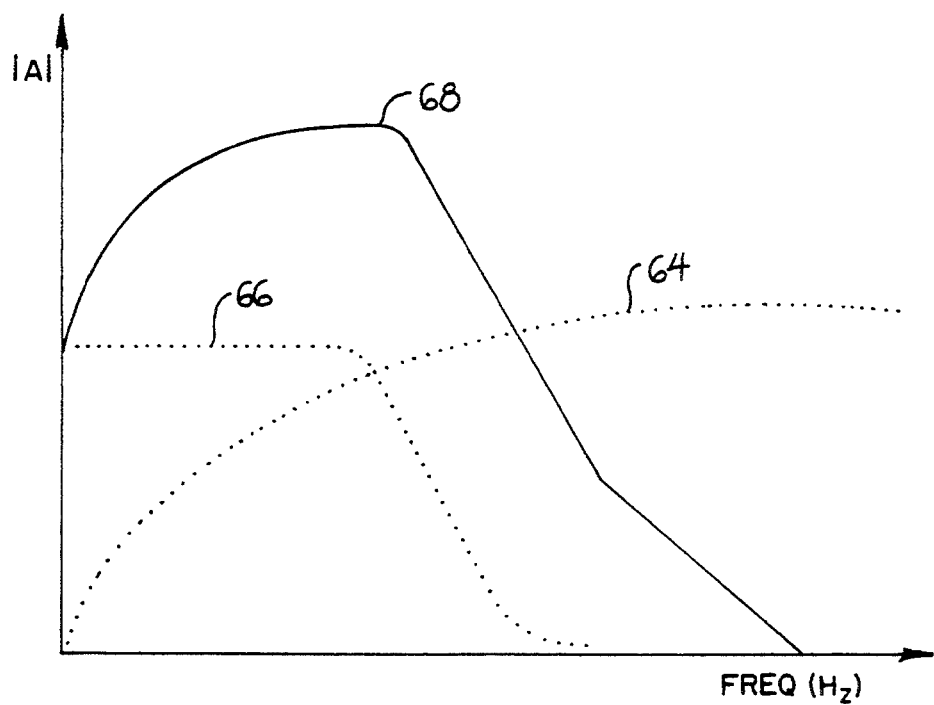
FIG. 3 is a plot of amplitude vs. the logarithm of frequency for the low-pass filter/differentiator for converting gradient input current to correlated noise reference signals.

Referring to FIG. 3, a derivative function may be approximated as a low-order, high-pass filter with a frequency response shown by dotted curve 64. The low pass filter of the studies amplifier 48 has a frequency response represented by dotted curve 66. A composite filter may be constructed having a frequency response 68 equal to the product of the frequency response 64 of the derivative function and the frequency response 66 of the studies amplifier 48, to provide a transfer function for receiving the waveform signals $G_x$, $G_y$, and $G_z$, and producing an approximation of the noise produced by the gradient coils 40. It will be apparent that for studies amplifiers 48 with different spectral characteristics, the frequency response 66 may be changed appropriately.

Figure 4:
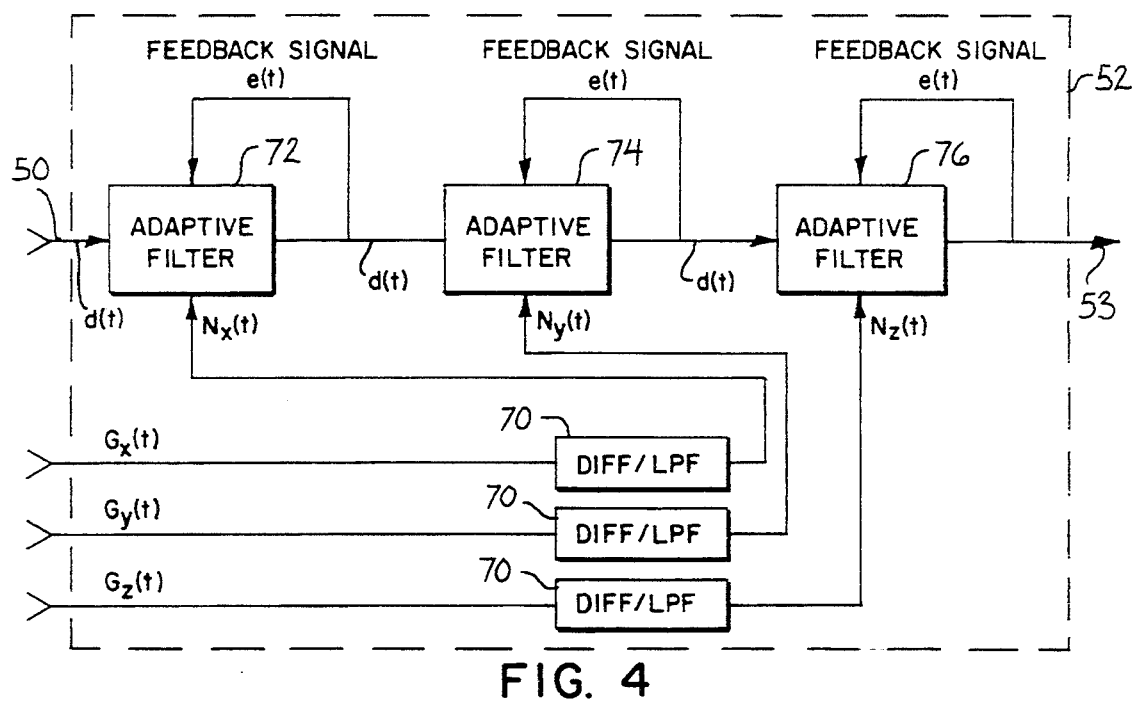
FIG. 4 is a block diagram of the signal processor of FIG. 1 showing the arrangement of the adaptive filters and the placement of the low-pass filter/differentiators of FIG. 3.

Referring now to FIGS. 1 and 4, the waveform signals $G_x$, $G_y$, and $G_z$ are received by the signal processor 52 and filtered by differentiator/low pass filters 70 ("Diff/LPF") having the spectral characteristics 68 previously described to produce correlated noise reference signals $N_x$, $N_y$, and $N_z$ from waveform signals $G_x$, $G_y$, or $G_z$ respectively. It has been determined that the value M of the mutual inductance of equations (1) and (2) above changes from patient to patient and from scan to scan. Hence, correlated noise reference signals $N_x$, $N_y$, and $N_z$ will not perfectly represent the induced noise on the bio-potential signal 50 nor are they easily combinable by any static method to produce an accurate noise signal.

Each correlated noise reference signal $N_x$, $N_y$, and $N_z$ is fed to one of three adaptive filters 72, 74, 76 connected in series for filtering the bio-potential signal 50. Specifically, the $N_x$ signal is connected to a first adaptive filter 72 that receives the bio-potential signal 50 from the studies amplifier 48. The output of this adaptive filter 72 is connected to the input of a second adaptive filter 74 which receives the correlated noise reference signal $N_y$. The output from the second adaptive filter 74 is received by the input of a third adaptive filter 76 which receives the correlated noise reference signal $N_z$. The output of the third adaptive filter 76 provides the output 53 of the signal processor 52 which equals the bio-potential signal 50 with reduced additive noise.

The adaptive filters 72, 74, and 76 modify the correlated noise reference signals $N_x$, $N_y$, and $N_z$ so that they match the actual additive noise produced by the gradient fields from the gradient coils 40. The adaptive filters 72, 74, and 76 have filter coefficients (not shown in FIG. 4) that are continually adjusted by reference to the output of that adaptive filter so as to minimize any noise related to the correlated noise reference signals $N_x$, $N_y$, and $N_z$ associated with that adaptive filter.

In an alternative embodiment (not shown) the waveform signals $G_x$, $G_y$, $G_z$ may be summed together and processed by a single differentiator/low pass filters 70 to produce a single correlated noise reference signal that is used by a single adaptive filter 72 which receives the bio-potential signal 50 and produces the output signal 53. The noise reduction of this method is less than that provided by three filters as described above.

Figure 5:
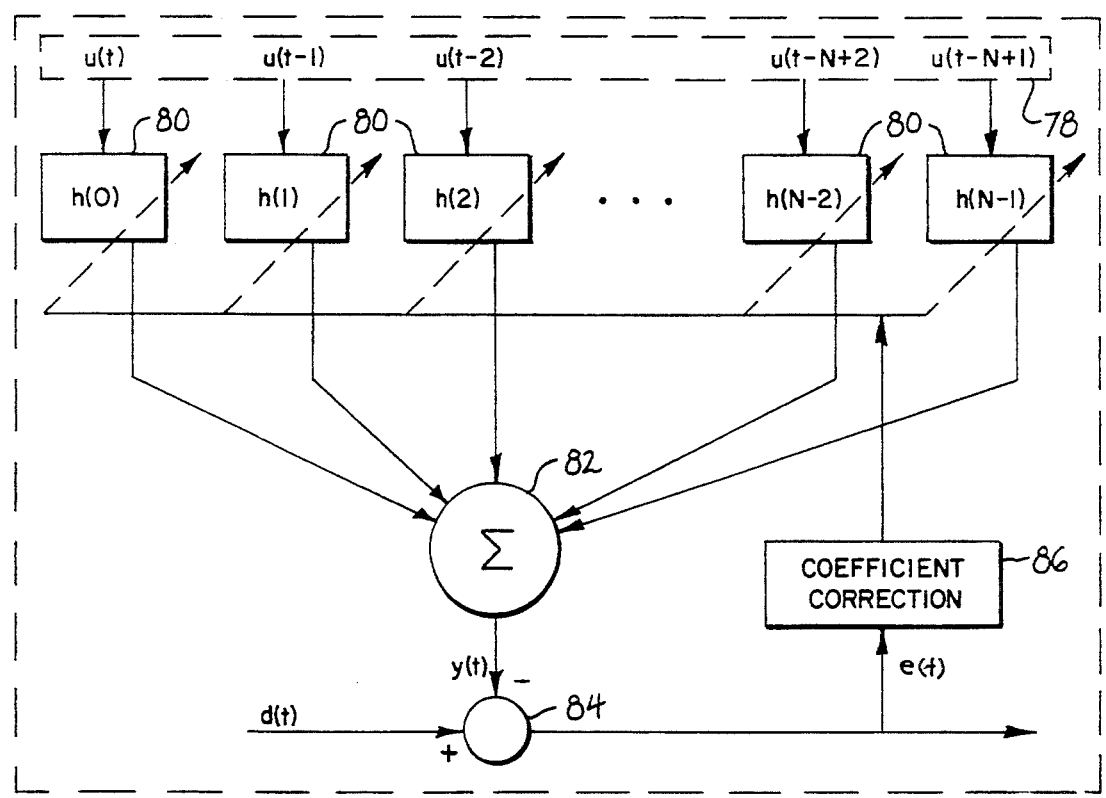
FIG. 5 is a block diagram of a representative adaptive filter of FIG. 4.

Referring to FIG. 5, each adaptive filter 72, 74, and 76 compiles a noise vector 78, comprised of a current sample of the correlated noise reference signal $N_x$, $N_y$ or $N_z$, associated with that filter and N-1 previous samples of that correlated noise reference signal taken at intervals dictated by the Nyquist sampling theorem. The current sample is designated u(t) and the least current sample is designated u(t−N+1). With each new sample u(t), the oldest sample is discarded so that the noise vector 78 comprises the most recent N samples on a rolling basis. In the present embodiment, the correlated noise reference signal is sampled at 1000 Hz and the number of samples, N, equals 16. As will be apparent from this description to one of ordinary skill in the art other sampling rates and numbers of samples may be used subject to the general guidelines that more samples and a higher sampling frequency will provide better filtering and more accurate representation of the signal but will require faster processing hardware.

Each of the samples of the noise vector 78 is weighted by a filter coefficient designated h(n) where n ranges from 0 to N−1 to correspond with the N samples of the noise vector. The weighting process, indicated by process blocks 80, multiplies each sample of the noise vector u by a corresponding filter coefficient h. The results of these multiplications are summed, as indicated by adder 82 to produce a filtered noise reference signal y(t) where:

$$y(t) = \sum_{k=0}^{k=N-1} [h(k)u(t-k)] \qquad (3)$$

This filtered noise reference signal y(t) is subtracted, as indicated by summing junction 84, from the input signal to the adaptive filter, d(t), which may be the bio-potential signal 50 or the output of a previous adaptive filter as shown in FIG. 4. The result of this subtraction forms the output from the adaptive filter, termed the error signal e(t), where:

$$e(t) = d(t) - y(t) \qquad (4)$$

The error signal e(t) is used to adapt the filter coefficients h(n) to the changes in the correlated noise reference signals, as shown by process block 86 according to the "least mean square" process as follows:

$$h'(n) = h(n) + \mu e(t)u(t) \qquad (5)$$

where h'(n) is the new filter coefficient, h(n) is the old filter coefficient and $\mu$ is a learning factor between 0 and 1 and in the preferred embodiment 0.001. The values N and $\mu$ control the accuracy of the filtering and the complexity of the signals that may be handled by the filter as is generally understood in the art.

Referring again to FIG. 4, the error signal e(t) for the final adaptive filter 76 in the series provides the output signal 53 from the signal processor 52. As will be apparent to one of ordinary skill in the art, the order of the adaptive filters 72, 74, and 76 may be changed without affecting the operation of the noise reduction.

The signal processor 52 receives a digital input 50 and produces a digital output 53 and the operations of the signal processor 52, as described above, are realized by a high speed digital signal processor board as is commercially available, based on the TMS-320C30 chip manufactured by Texas Instruments and operating in conjunction with a microprocessor based computer ("PC") The digital signal processor provides 32-bit floating point manipulation of digitized analog signals on a real time basis.

Figure 6:
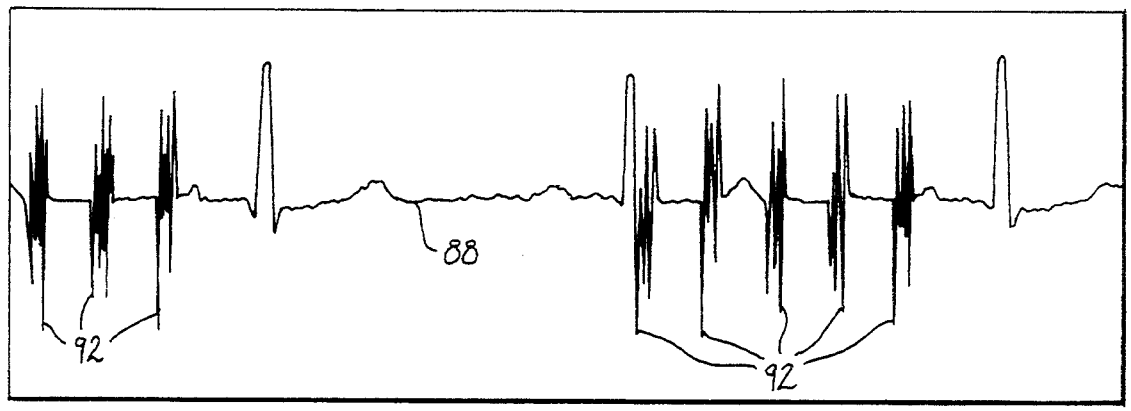
FIG. 6 is a plot of an ECG signal corrupted with gradient induced noise.
Figure 7:
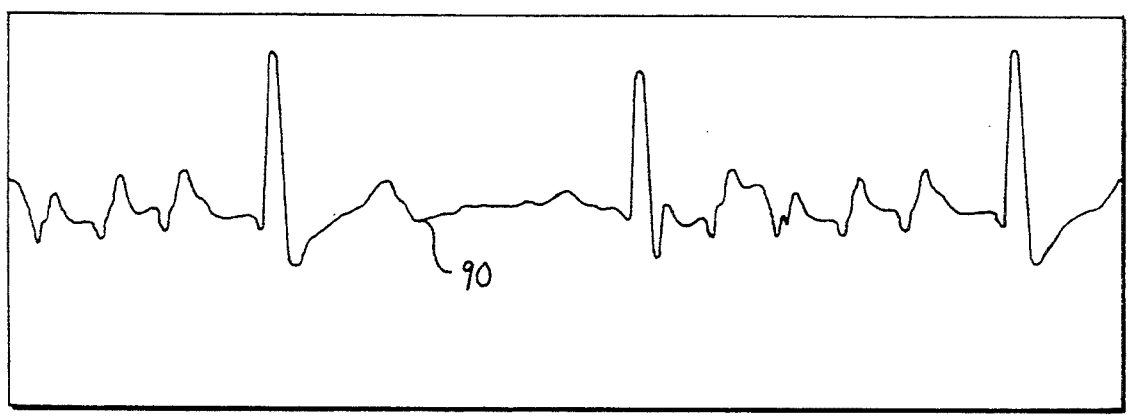
FIG. 7 is a plot of the signal of FIG. 6 after processing by the present invention.

Referring to FIG. 6, an example ECG signal 88 taken during an MR scan is shown having noise pulses 92. The same ECG signal 90 after the processing of the signal processor 52 shows substantial reduction in noise pulses.

The above description has been that of a preferred embodiment of the present invention. It will occur to those who practice the art that many modifications may be made without departing from the spirit and scope of the invention. For example, other bio-potential signals than ECG may be processed by the invention including EEG signals. Also, the noise reference signals $N_x$, $N_y$, and $N_z$ may be derived from sources other than the inputs to the gradient amplifiers, for example, from a pick up coil placed near the patient 12. The noise reduction of the present invention also is equally applicable to electromagnetic interference produced by the MRI equipment where a correlated noise reference signal may be obtained. In order to apprise the public of the various embodiments that may fall within the scope of the invention, the following claims are made.

We claim:

1. A signal processor for bio-potential signals acquired during the operation of magnetic resonance imaging equipment and having an added noise signal formed of multiple noise components from corresponding multiple coils associated with the magnetic resonance imaging equipment, each coil having a corresponding electrical input for producing its magnetic field, the signal processor comprising:

noise means for generating a noise reference signal for each coil correlated to the noise component associated with that coil;

an adaptive filter unit for each coil and having inputs for receiving the noise reference signal for that coil and the bio-potential signal plus at least one noise component and having an output for producing an output signal, each adaptive filter comprising:

filters having coefficients and for filtering the noise reference signals to produce a filtered noise reference signal for each coil approximating the noise component associated with the respective coil;

summing junctions associated with each filter for receiving the filtered noise reference signal and the bio-potential signal and for producing the output signal.

adapters for receiving the output signal from each summing junction and for adjusting the coefficients of the filter associated with the summing junction to separately minimize each output signal;

the output signals being combined to produce a noise reduced signal substantially equal to the bio-potential signal without the added noise signal.

2. The signal processor of claim 1 wherein the summing junctions are combined in series with the first summing junction of the series receiving the bio-potential signal as its input signal, each successive summing junction receiving the output signal from the previous summing junction as its input signal and the output signal of the final summing junction forming the noise reduced signal.

* * * * *